(12) United States Patent
Mantri et al.

(10) Patent No.: US 11,751,846 B2
(45) Date of Patent: Sep. 12, 2023

(54) STIFF SHEATH FOR IMAGING PROBE

(71) Applicant: PROCEPT BioRobotics Corporation, Redwood City, CA (US)

(72) Inventors: Surag Mantri, East Palo Alto, CA (US); Kevin Patrick Staid, Lowell, MA (US)

(73) Assignee: PROCEPT BioRobotics Corporation, Redwood City, CA (US)

( * ) Notice: Subject to any disclaimer, the term of this patent is extended or adjusted under 35 U.S.C. 154(b) by 0 days.

(21) Appl. No.: 17/247,922

(22) Filed: Dec. 30, 2020

(65) Prior Publication Data
US 2021/0113184 A1 Apr. 22, 2021

Related U.S. Application Data

(63) Continuation of application No. PCT/US2020/021708, filed on Mar. 9, 2020.

(60) Provisional application No. 62/815,331, filed on Mar. 7, 2019.

(51) Int. Cl.
*A61B 8/00* (2006.01)

(52) U.S. Cl.
CPC ............ *A61B 8/445* (2013.01); *A61B 8/4455* (2013.01)

(58) Field of Classification Search
CPC ........ A61B 8/445; A61B 8/4455; A61B 1/015
See application file for complete search history.

(56) References Cited

U.S. PATENT DOCUMENTS

| | | | | |
|---|---|---|---|---|
| 5,400,767 A | * | 3/1995 | Murdoch | A61B 1/313 600/157 |
| 5,437,283 A | * | 8/1995 | Ranalletta | A61B 8/4488 600/463 |
| 5,469,853 A | | 11/1995 | Law | |
| 5,762,066 A | * | 6/1998 | Law | A61B 8/12 601/3 |
| 6,120,434 A | | 9/2000 | Kimura | |
| 6,319,235 B1 | * | 11/2001 | Yoshino | A61B 5/150519 604/212 |
| 6,354,992 B1 | * | 3/2002 | Kato | A61B 1/126 600/157 |

(Continued)

FOREIGN PATENT DOCUMENTS

| | | |
|---|---|---|
| JP | H06261905 | 9/1994 |
| WO | 2008083407 | 7/2008 |

(Continued)

OTHER PUBLICATIONS

International Search Report and Written Opinion for International Application No. PCT/US2020/021708, 14 pages (dated Jul. 27, 2020.

*Primary Examiner* — Angela M Hoffa
*Assistant Examiner* — Younhee Choi
(74) *Attorney, Agent, or Firm* — FISHERBROYLES LLP; John Shimmick

(57) ABSTRACT

An imaging probe is covered with a stiff sheath, which allows the imaging probe to move while the stiff sheath remains in a substantially fixed location for at least a portion of the surgical procedure while the probe moves within the stiff sheath. The stiff sheath may comprise sufficient stiffness to resist deformation as the imaging probe moves along an internal channel of the sheath. The sheath can be sized and shaped in many ways and may comprise one or more openings to allow fluid to move within the channel in which the probe is located.

20 Claims, 8 Drawing Sheets

(56) References Cited

U.S. PATENT DOCUMENTS

| | | | |
|---|---|---|---|
| 7,882,841 B2 | 2/2011 | Aljuri | |
| 8,814,921 B2 | 8/2014 | Aljuri | |
| 9,232,959 B2 | 1/2016 | Aljuri | |
| 2007/0293761 A1* | 12/2007 | Wickline | A61B 8/12 600/459 |
| 2010/0152590 A1* | 6/2010 | Moore | A61B 8/4461 600/466 |
| 2010/0168510 A1* | 7/2010 | Rogers | A61B 17/29 600/104 |
| 2012/0253197 A1* | 10/2012 | Sadaka | A61B 8/12 600/444 |
| 2014/0257105 A1* | 9/2014 | Dausch | A61B 8/4281 600/458 |
| 2015/0057646 A1* | 2/2015 | Aljuri | A61B 34/25 606/10 |
| 2015/0088107 A1 | 3/2015 | Aljuri | |
| 2018/0263647 A1 | 9/2018 | Aljuri | |
| 2018/0353057 A1 | 12/2018 | Cheng | |
| 2019/0029750 A1* | 1/2019 | Maini | A61B 8/12 |

FOREIGN PATENT DOCUMENTS

| | | |
|---|---|---|
| WO | 2009111736 | 9/2009 |
| WO | 2011097505 | 8/2011 |
| WO | 2013130895 | 9/2013 |
| WO | 2014127242 | 8/2014 |
| WO | 2014165703 | 10/2014 |
| WO | 2015035249 | 3/2015 |
| WO | 2015200538 | 12/2015 |
| WO | 2016004071 | 1/2016 |
| WO | 2016037132 | 3/2016 |
| WO | 2016037137 | 3/2016 |
| WO | 2017161331 | 9/2017 |
| WO | 2019032986 | 2/2019 |
| WO | 2019246580 | 12/2019 |
| WO | 2020180724 | 9/2020 |
| WO | 2020181278 | 9/2020 |
| WO | 2020181280 | 9/2020 |
| WO | 2020181281 | 9/2020 |
| WO | 2020181290 | 9/2020 |

* cited by examiner

STIFF SHEATH FOR IMAGING PROBE

RELATED APPLICATIONS

This application is a bypass continuation of International Application No. PCT/US2020/021708, filed Mar. 9, 2020, published as WO 2020/181280 on Sep. 10, 2020, and claims the benefit under 35 U.S.C. § 119(e) of U.S. Provisional Patent Application No. 62/815,331, filed Mar. 7, 2019, entitled STIFF SHEATH FOR IMAGING PROBE, the entire disclosures of which are incorporated herein by reference.

BACKGROUND

Work in relation to the present disclosure suggests that prior methods and apparatus to image tissue with a probe inserted into the patient can be less than ideal in at least some instances. For example, movement of the probe can result in movement of tissue. With some surgical applications, it would be helpful to accurately align the surgical treatment with images obtained during the surgical procedure. Some imaging probes such as a trans-rectal ultrasound ("TRUS") probe can move along an elongate axis of the probe to image the patient. Movement of the imaging probe can result in movement of the target tissue, which can make registration of the targeted tissue with actual position of the tissue less than ideal. For example, some prior approaches have relied on a soft sheath covering the TRUS probe, and movement of the TRUS probe within the stiff sheath can move the target tissue and affect the quality of imaging in at least some instances.

Although a stiff sheath for use with a TRUS probe has been proposed previously, further improvements would be helpful. For example, bubbles can form within the sheath during imaging, which can degrade the quality of the images obtained with the TRUS probe. With some types of surgery such as prostate surgery, the treated tissue is imaged on an upper side of the probe while the patient is reclined in a nearly supine position. Work in relation to the present disclosure suggests that bubbles may appear on an upper side of the probe between the probe and the imaged tissue, which can degrade images of tissue such as the prostate in at least some instances.

SUMMARY

The presently disclosed methods and apparatuses can provide improved imaging with decreased bubble formation. In some embodiments, an imaging probe is covered with a stiff sheath, which allows the imaging probe to move while the stiff sheath remains in a substantially fixed location for at least a portion of the surgical procedure while the probe moves within the stiff sheath. The stiff sheath may comprise sufficient stiffness to resist deformation as the imaging probe moves along an internal channel of the sheath. In some embodiments the sheath comprises one or more structures to collect gas and remove bubbles. The sheath may comprise an internal outlet channel to direct fluid from near a tip of the sheath to a proximal portion of the sheath. In some embodiments, the internal outlet channel is located on a lower portion of the probe to direct bubbles away from the upper side of the probe. Alternatively or in combination, an outlet channel such as vent channel can be located on an upper side of the sheath toward a proximal end of the sheath. The probe can be pointed downward and the TRUS probe moved within the sheath to move bubbles toward the outlet channel such as the vent channel for removal.

In some embodiments, the sheath comprises a stiff distal portion and a compliant proximal portion, in which the compliant proximal portion is configured to expand and contract as the TRUS probe moves distally and proximally, respectively. In some embodiments, the proximal portion comprises a seal configured to engage the TRUS probe to decrease leakage from the TRUS sheath.

The sheath can be sized and shaped in many ways, and may comprise one or more openings to allow fluid to move within the channel in which the probe is located. In some embodiments, the sheath comprises a plurality of openings to allow fluid to move in and out of the channel, and may comprise a mesh or other support structure configured to retain imaged tissue while the probe moves within the sheath, which allows the tissue to be imaged more accurately. In some embodiments, the imaging probe comprises a TRUS probe comprising an elongate axis, and the sheath comprises an elongate axis defining an elongate channel along which the TRUS probe moves. The sheath may comprise a proximal end configured to be attached to a support configured not to move while the TRUS probe moves within the patient.

In some embodiments, a surgical system comprises an imaging probe and a treatment probe, in which the imaging probe and the treatment probe are configured to move, for example synchronously, while the sheath is configured to remain substantially fixed. This arrangement allows the imaging and treatment probes to move and decreases movement of tissue during imaging and treatment, which can improve the accuracy of tissue resection such as tissue treatment. The imaging probe may comprise a TRUS probe and the surgical probe may comprise a urological probe configured to be advanced from a distal and external end of the urethra to a prostate of the patient.

INCORPORATION BY REFERENCE

All patents, applications, and publications referred to and identified herein are hereby incorporated by reference in their entirety, and shall be considered fully incorporated by reference even though referred to elsewhere in the application.

The subject matter of the following patents is related to the present disclosure: U.S. Pat. No. 8,814,921, issued Aug. 26, 2014, entitled "TISSUE ABLATION AND CAUTERY WITH OPTICAL ENERGY CARRIED IN FLUID STREAM"; U.S. Pat. No. 9,232,959, issued Jan. 12, 2016, entitled "MULTI FLUID TISSUE RESECTION METHODS AND DEVICES"; U.S. Pat. No. 7,882,841, issued Feb. 8, 2011, entitled "MINIMALLY INVASIVE METHODS AND DEVICES FOR THE TREATMENT OF PROSTATE DISEASES"; International Application No. PCT/US2011/023781, filed Apr. 8, 2007, published as WO2011097505 on Nov. 8, 2011, entitled "MULTI FLUID TISSUE RESECTION METHODS AND DEVICES"; International Application No. PCT/US/2013/028441, filed Feb. 28, 2013, published as WO2013/130895 on Sep. 6, 2013 entitled "AUTOMATED IMAGE-GUIDED TISSUE RESETION AND TREATMENT"; and International Application No. PCT/US2014/054412, filed Sep. 5, 2014, published as WO2015/035249 on Mar. 12, 2015, entitled "AUTOMATED IMAGE-GUIDED TISSUE RESETION AND TREATMENT", the entire disclosures of which are incorporated herein by reference.

BRIEF DESCRIPTION OF THE DRAWINGS

A better understanding of the features, advantages and principles of the present disclosure will be obtained by reference to the following detailed description that sets forth illustrative embodiments, and the accompanying drawings of which.

DETAILED DESCRIPTION

Figure 1:
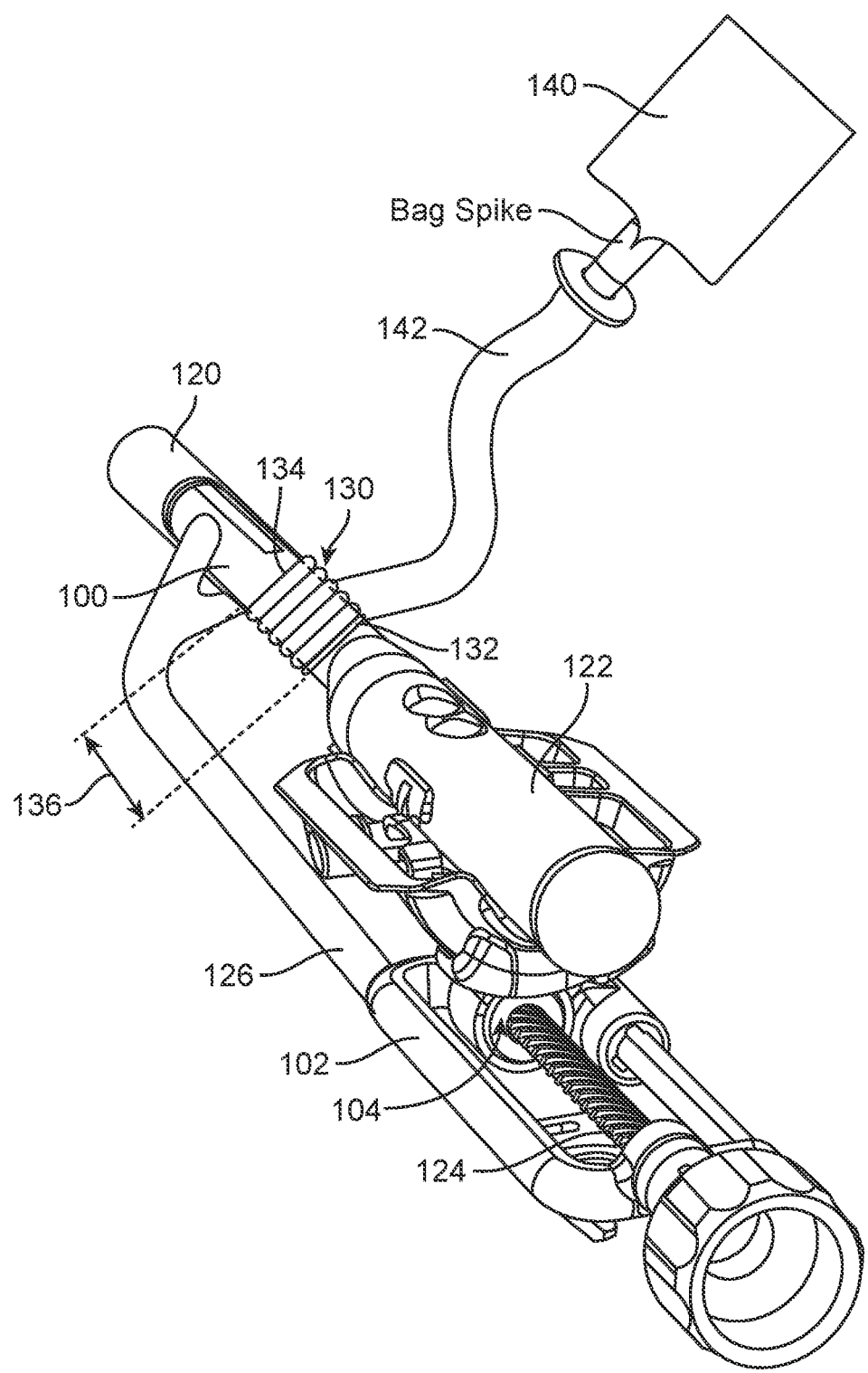
FIG. 1 shows an imaging probe in a stiff sheath, in accordance with some embodiments.

The following detailed description provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

While embodiments of the present disclosure are specifically directed to treatment of the prostate, certain aspects of the disclosure may also be used to treat and modify other organs such as brain, heart, lungs, intestines, eyes, skin, kidney, liver, pancreas, stomach, uterus, ovaries, testicles, bladder, ear, nose, mouth, soft tissues such as bone marrow, adipose tissue, muscle, glandular and mucosal tissue, spinal and nerve tissue, cartilage, hard biological tissues such as teeth, bone, as well as body lumens and passages such as the sinuses, ureter, colon, esophagus, lung passages, blood vessels, and throat. The devices disclosed herein may be inserted through an existing body lumen, or inserted through an opening created in body tissue.

The stiff sheath can be configured in many ways. In some embodiments, the sheath keeps an organ such as the prostate substantially immobile while the imaging probe moves. The imaging probe can be moved along an elongate axis of the imaging probe and an elongate axis of the sheath while the sheath substantially immobilizes the imaged tissue. Alternatively or in combination, the imaging probe can be rotated about the elongate axis. The imaging probe can be moved with rotation and translation to generate a 3D tomographic image of the tissue of the organ, such as a 3D volumetric image of the tissue of the prostate. The sheath can retain the imaged tissue in substantially the same location while the imaging probe moves within the sheath. The image of the tissue of the organ can be obtained.

The ultrasound transducer may comprise any suitable transducer, and the imaged tissue may comprise any suitable tissue as described herein. The stiff sheath can provide increased movement of the probe at greater speed and frequencies, which can be helpful to real time imaging. The ultrasound transducer elements may comprise an array of ultrasound crystals, e.g. a linear array, or a rotating single transducer element with coordinated image generation. For example, a rotation single transducer can be rotated and translated with sufficient speed to provide volumetric 3D imaging of the tissue. Alternatively, a plurality of ultrasound crystals can be employed. In some embodiments, the ultrasound probe comprises a TRUS probe rotated to provide 3D volumetric imaging of the tissue. In some embodiments, sagittal array of the ultrasound probe is rotated to obtain 3D images. While the probe can be rotated about an elongate axis of the sheath with many angles, the amount of rotation can with within a range from about 45 degrees to 135 degrees, for example from 45 degrees to 90 degrees.

In some embodiments, the treatment probe has been placed in the patient prior to imaging the tissue with the imaging probe and the sheath, which can further decrease movement of the tissue. The treatment probe may comprise an internal carrier that moves independently relative to the external sheath and the imaging probe, for example with rotation, translation and oscillation of the carrier relative to the imaging probe and sheath. The carrier may comprise an energy source, such as a water jet, that can be moved independently in relation to the imaging probe and sheath.

An image of the tissue to be treated can be shown on a display, and the user such as a surgeon can input the treatment parameters in response to the image of the tissue of the patient shown on the display.

The sheath may be configured to contain an internal flowable material, such as a fluid, a gel, or saline. In some embodiments, the fluid comprises saline, and the internal channel may be coupled to an external reservoir to provide flowable material such as a gel or a liquid such as saline as the probe translates within the sheath. In some embodiments, saline coupled to the internal channel of the sheath allows smaller internal diameter of the sheath, which can be related to the decreased viscosity of a liquid such as saline compared to the viscosity of a gel. In some embodiments, a gel source is alternatively or additionally in communication with the channel of the sheath and can provide additional fluid, such as for ultrasound imaging. The flowable material source, e.g. ultrasound gel source, may comprise a syringe that is adapted to inject and/or withdraw gel from within the sheath. In some embodiments, the gel source provides a reservoir of gel that is drawn into the sheath when the probe is retracted due to a lower pressure within the sheath created as the probe is retracted. Conversely, as the probe is advanced into the sheath, gel within the sheath may be forced into the gel source due to the increased fluid pressure from the probe being inserted into the sheath.

In some embodiments, the sheath comprises an ultrasound index of refraction and acoustic impedance similar to an acoustic impedance of the imaged tissue. Alternatively or in combination, the sheath may comprise an internal diameter sized slightly larger than the imaging probe, such that reflected acoustic waves can be more readily filtered than with a larger distance between the sheath and the probe. In some embodiments, the difference in diameter between the imaging probe and the internal surface of the sheath is on the order of 0.25 mm, 0.5 mm, 1 mm, 2 mm, 3 mm, 4 mm, or 5 mm or more, or within a range defined by any two of the preceding values.

The sheath may be formed of any suitable material, but in some embodiments, is formed from a material selected for its ultrasonic properties having a desired refractive index, absorption, and transmittance, e.g. to substantially match the issue being imaged. Work in relation to the present disclosure suggests that a smooth sheath can provide improved imaging, with less reliance on ultrasound signal filtering and decreased gap distance as described herein.

FIG. 1 illustrates a probe 100, such as a TRUS probe. The probe 100 may be mounted to a supporting base structure 102. The base structure 102 can be coupled to an arm or other suitable support configured to maintain placement of the stiff sheath 120 in the patient. The probe 100 may comprise a track or a guide 104 to facilitate translational motion of the probe 100 while the probe moves independently of the sheath 120. In some embodiments, the supporting base structure 102 is coupled to an arm 126 that supports the stiff sheath. The stiff sheath 120 is coupled to the base structure 102 and arm 126 to remain in a substantially fixed position while the imaging probe moves within the sheath 120. The imaging probe 100 may comprise a linkage and motors 122 coupled to the base structure 102 to move the imaging probe 100 under processor control while the sheath 120 remains substantially fixed. In some embodiments, a motor 122 facilitates translational motion of the probe 100, and may be configured to turn a power screw 124 to advance or withdraw the probe 100. A stepper motor 122 may be used for translational motion of the probe 100 due to its accuracy and repeatability. Additional motors can be coupled to the base structure 102 to provide rotational movement to the probe 100 about the elongate axis of the probe.

In some embodiments, the probe 100 is configured to be positioned within a patient, and the motor 122 can accurately and repeatably translate the probe 100 proximate to an imaging or a treatment location within the patient. Moreover, the motor 122 is able to translate the probe 100 during imaging or between sequential images to capture multiple images, such as for tomography.

Another actuator, such as a motor, may be operatively coupled to the probe 100 to rotate the probe to orient the imaging sensors of the probe relative to a target area, or to optionally rotate the probe 100 during image capture or between successive image captures to create multiple images of a target site.

A sheath 120 may be disposed over the probe 100, which may be a stiff, or rigid, sheath. As used herein, the terms "stiff" and "rigid" may be used interchangeably and are used to refer to a material that is able to withstand compressive forces resulting from being placed inside a patient and contacting tissue therein. Additionally, the stiff sheath 120 is preferably able to withstand an internal pressure differential caused by advancing or withdrawing the probe 100 within the sheath 120 without substantially deforming in response to the applied forces. In this way, the stiff sheath 120, once inserted into a patient, provides support to the surrounding tissue in contact with the sheath 120 and maintains the tissue in a static position with respect to the sheath 120 during imaging.

In use, the probe 100 is configured to translate and/or rotate relative to the sheath 120 to capture images or provide treatment. In some embodiments, translation of the probe 100 does not disturb the surrounding tissue so that successive images can be accurately captured, such as for assembling into a three-dimensional image or model of the target area.

The stiff sheath 120 may be coupled to the probe 100, the motor 122, or base 102, or an arm 126 disposed between the base 102 and the motor 122 through any suitable connection method. In some embodiments, the sheath 120 is coupled to a proximal portion of the probe through a flexible coupling 130 to provide for extension, retraction, and/or rotation of the probe 100 relative to the sheath 120.

In some embodiments, the flexible coupling 130 is formed of an elastomeric material that is able to deform to allow for the relative motion between the probe 100 and the sheath 120. In some embodiments, the flexible coupling 130 is shaped as a bellows to accommodate the relative motion, although other shapes can be used such as balloon shapes. The flexible coupling 130 is coupled to the stiff sheath near a distal end 134 of the flexible coupling. The distal end of the flexible coupling is coupled to the sheath so as to inhibit leakage of flowable material between the stiff sheath 134 and the flexible coupling. The flexible coupling 130 comprises a seal 132 to engage the probe 100. A distance 136 extends between the seal 132 and the distal end of the flexible coupling. In some embodiments the distance 136 changes when the probe 100 is advanced and retracted from stiff sheath 120. For example distance 136 can decrease when the probe 100 is advanced distally and distance 136 can increase when probe 100 is drawn proximally.

In some embodiments, the stiff sheath 120 comprises the same material as the flexible coupling 130 and may be formed from an integrated single piece component, e.g. a single piece molded component. Alternatively, the flexible coupling 130 may comprise a different material (e.g. an elastomer) from the stiff sheath 120, which may comprise a stiffer plastic or harder silicone, for example. In some embodiments the coupling 130 is adhered to the stiff sheath 120, for example by welding or an adhesive.

In some embodiments, the flexible coupling 130 comprises a seal 132. The seal 132 may remain fixed relative to the stiff sheath 120 and slides along the imaging probe 100. In some embodiments, the sliding seal 132 comprises a piston seal that slides along the probe 100 when the probe is advanced and retracted. In some embodiments, the flexible coupling 130 comprises a seal 132 that remains fixed to the imaging probe 100 while the imaging probe moves. For example, the flexible seal 132 may comprise an elastomeric band that holds the seal 132 on the probe 100 with pressure, such that seal 132 moves with probe 100, while distal end 134 remains fixed.

While the flexible coupling 130 can be configured in many ways, in some embodiments the flexible coupling 130 comprises a reservoir to store a volume of flowable material. The volume of flowable material within the flexible coupling 130 can change with movement of the probe 100 within the stiff sheath 120. For example, movement of the probe 100 proximally within rigid sheath 120 can draw flowable material into the stiff sheath from the coupling 130. Movement of the probe 100 distally within rigid sheath 120 can push flowable material from the stiff sheath into the coupling 130. In some embodiments, the flexible coupling 130 is fluidically coupled to a fluid source 140. In some embodiments, the flowable material flows from the flexible coupling 130 into a fluid source 140 and vice versa. Alternatively or in combination, the flexible coupling 130 may comprise a variable volume reservoir, such that the volume of flowable material in the flexible coupling 130 increases when the probe 100 advances distally within sheath 120 and the volume within flexible coupling 130 decreases when the probe 100 is drawn proximally within sheath 120.

In some embodiments, the flexible coupling 130 comprises a balloon configured to inflate with flowable material when probe 100 advances into sheath 120 and to deflate when probe 100 retracts proximally within sheath 120. The balloon may comprise a compliant or a non-complaint balloon, for example. The balloon may comprise an elastomeric portion to seal against the probe 100 and move with the probe 100 while the distal end of the coupling 130 remains fixed to the stiff sheath 120.

In some embodiments, a source 140 of flowable material, such as a gel, fluid, or liquid is in fluid communication with the channel formed within the sheath 120 to provide flowable material, e.g. fluid or gel, to the interior portion of the sheath 120. The fluid source may comprise ultrasound gel or saline solution, or another solution that may be advantageously introduced to the interior of the sheath 120, such as to aid in motion, positioning, rotation, imaging, or another purpose. The fluid source 140 may be coupled to the flexible coupling 130 through any suitable fluid-tight seal, which may additionally include a bifurcate structure to allow multiple fluid paths, such as for injection of fluid and to vent gas or fluid from within the sheath 120. Alternatively, the fluid source 140 and its concomitant fluid line 142 may provide both the fluid fill and vent pathways.

In addition, or alternatively, a gel source may be provided and be in fluid communication with the interior of the sheath 120. The gel source 140 may provide a gel to the interior of the sheath 120 to aid in motion, positioning, rotation, imaging, or another purpose.

In some embodiments, the sheath 120 is coupled to the apparatus to provide a fluid-tight seal to inhibit fluid within the sheath from leaking. The fluid-tight seal 132 may be any suitable seal that provides a fluid tight seal between the coupling of the sheath and the probe, and may be a type of band clamp causing compression of the coupling in a radial inward direction and may be formed of one or more material such as elastics, metallics, plastics, or any combination. The sheath 120 may be coupled to the probe 100, the motor 122, the arm 126, or the base 102.

In some embodiments, the sheath 120 has openings therein to allow direct access for further treatment at the treatment site. For example, one or more openings may be provided in the sheath 120 to allow alternative probes to be presented to the treatment site such as probes for aspiration, tissue resection and collection, cautery probes such as electro-cautery.

In some embodiments, the openings within the sheath are selectively openable, thereby providing a fluid-tight seal when closed, and optionally being openable to allow direct access to a treatment site. The selective openings in the sheath may comprise a hinged access cover, a slidable access cover which may be slidable in a translational direction or a radial direction, or an area of weakness that may be penetrated.

Selectively openable apertures in the sheath allow the sheath to present a contiguous outer surface during insertion in a patient to inhibit the sheath catching on any external obstructions yet is able to provide openings for direct site access through the selectively openable apertures.

In embodiments, the resulting images may be post processed to correct for distortions resulting from capturing images through the sheath and through distortions such as openings. For example, images captured through the opening may exhibit distortions due to differing ultrasound refractory indexes and acoustic impedance between the sheath and the openings.

Figure 2:
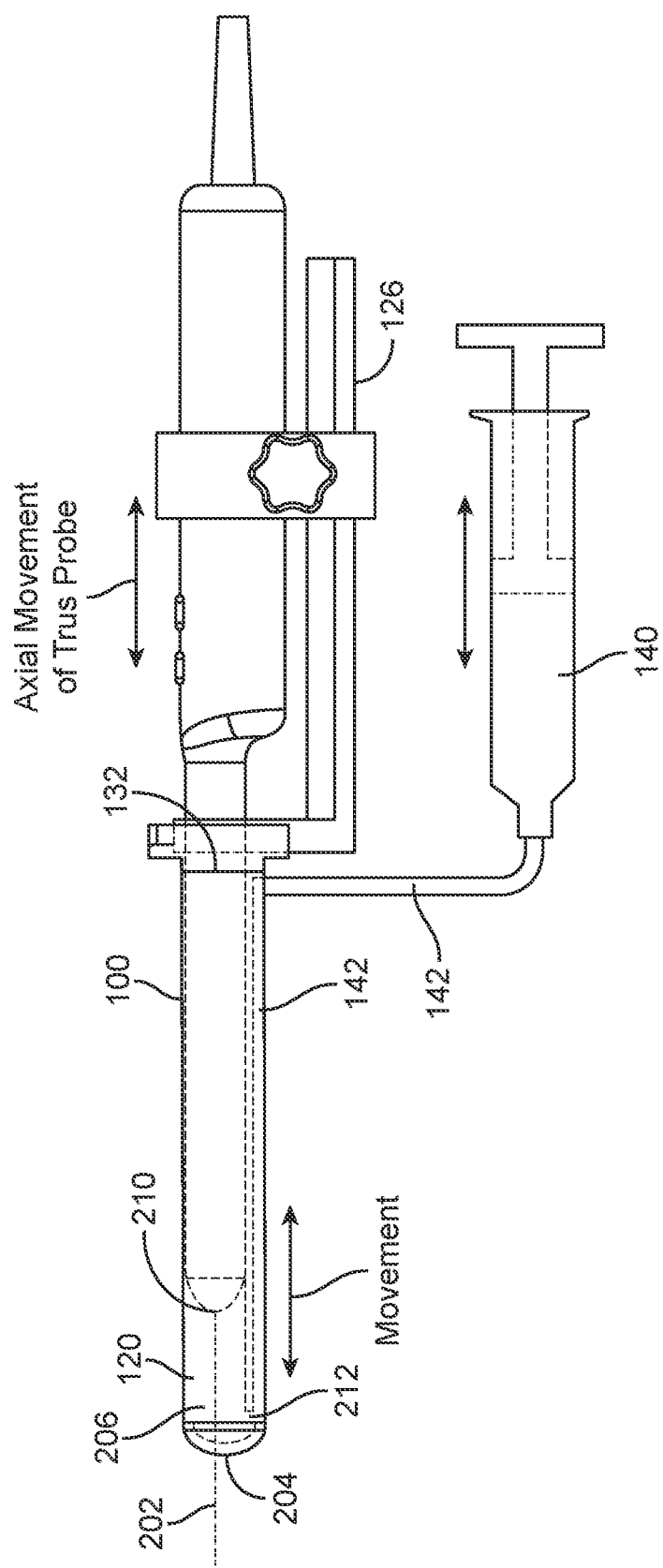
FIGS. 2 and 3 show a side view and an isometric view, respectively, of a stiff sheath over a transrectal ultrasound probe to inhibit changes in tissue shape as the elongate ultrasound probe moves along an elongate axis of the ultrasound probe, in accordance with some embodiments.
Figure 3:
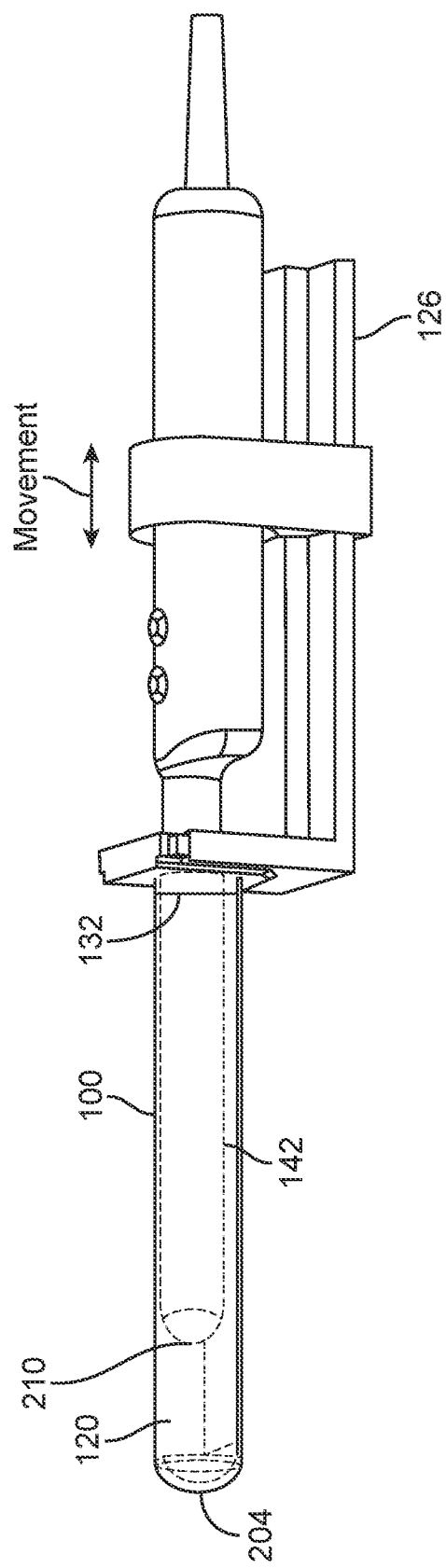

FIGS. 2 and 3 show a side view and an isometric view, respectively, of a stiff sheath 120 over a transrectal ultrasound probe 100 to inhibit changes in tissue shape as the elongate ultrasound probe 100 moves along an elongate axis 202 of the ultrasound probe 100. The stiff sheath 120 comprises a seal 132 to inhibit leakage as described herein. In some embodiments, the seal 132 is formed with the inner dimension of the stiff sheath and outer dimension of the probe 100 sized to form a seal. The stiff sheath 120 can be combined with other components as described herein. Insertion of the imaging probe 100 into the patient can induce changes in the shape of the tissue when the probe is advanced. A stiff sheath 120 can be provided on the imaging probe 100 such that the shape of the prostate and tissue near the prostate is not altered by axial movement of the imaging probe 100 along an elongate axis 202 of the imaging probe when the sheath 120 remains substantially fixed. Once inserted, the imaging probe 100 can be moved axially independently with respect to the stiff sheath 120 that engages the colon of the patient. As the stiff sheath 120 engages the wall of the colon of the patient and separates the imaging probe 100 from the wall of the colon, the imaging probe 100 can be moved axially without altering the shape of the patient tissue near the probe, such as the tissue of the prostate, for example.

The stiff sheath 120 comprises a rounded distal end portion 204 that can be spherical or oval in shape for advancement into the patient. The distal end portion 204 can be stiff, or designed to deflect slightly when advanced, for example. The stiff sheath 120 may comprise at least a tubular portion that has stiffness to add rigidity and define a chamber 206 within the sheath 120 when an imaging probe distal end 210 is away from the sheath distal end portion 204. The chamber 206 extends axially between the imaging probe distal end 210 and the sheath distal end portion 204, and radially between the cylindrical side of the sheath 120.

The elongate axis 202 of the stiff sheath 120 and the imaging probe 100 can be aligned with the elongate axis of a treatment probe. The stiff sheath 120 can be fixed to a locking arm 126, and the locking arm may additionally be coupled to the imaging probe 100.

The stiff sheath 120 can be configured to provide ultrasonic coupling material between the sheath 120 and the imaging probe 100 to provide ultrasonic coupling of the imaging probe to the prostate tissue with the stiff sheath 120 extending therebetween. The chamber 206 of the sheath 120 comprises a container having a variable volume as the imaging probe 100 is moved axially. As the imaging probe 100 is advanced distally, the volume of the chamber 206 decreases. As the imaging probe 100 is retracted proximally, the volume of the chamber 206 defined with the sheath 120 and the imaging probe 100 increases.

A fluidic coupling channel 142 is provided to couple fluid of the chamber 206 within the sheath to a fluid source 140, such that ultrasound coupling fluid can be contained within the sheath 120 as the volume changes. The fluid source 140 may comprise a sealed container, such as a bag or syringe, for example. The fluid source 140 may be configured to provide a variable volume and remain sealed, for example. In some embodiments, the fluid source 140 provides a closed fluid system between the fluid source, the fluidic coupling channel 142, and the chamber 206. The coupling channel 142 may comprise an external channel outside the sheath 120, such as a tube, or an internal channel within the sheath 120 such as an inner channel defined with an inner wall of the stiff sheath 120, and combinations thereof. The inner wall of the stiff sheath may comprise a stiff barrier material that defines the coupling channel 142, for example. Alternatively or in combination, the inner channel may comprise a groove on an inner surface of the stiff sheath 120 to allow ultrasound coupling material to flow between the imaging probe 100 and the stiff sheath 120. The coupling channel 142 may extend to an opening 212 near the distal end of the stiff sheath, such that the distal end of the imaging probe 100 can be placed near the distal end of the stiff sheath 120. The opening 212 of the coupling channel communicates with the interior of the stiff sheath 120 at a location between the closed end 204 and the seal 132.

In some embodiments, axial movement of the imaging probe 100 is provided by axial movement of the linkage as described herein, such as by a motor operatively coupled to a power screw. The axial movement of the imaging probe 100 provided by linkage results in axial movement of the distal end 210 of the imaging probe in relation to the sheath distal end portion 204.

Figure 4:
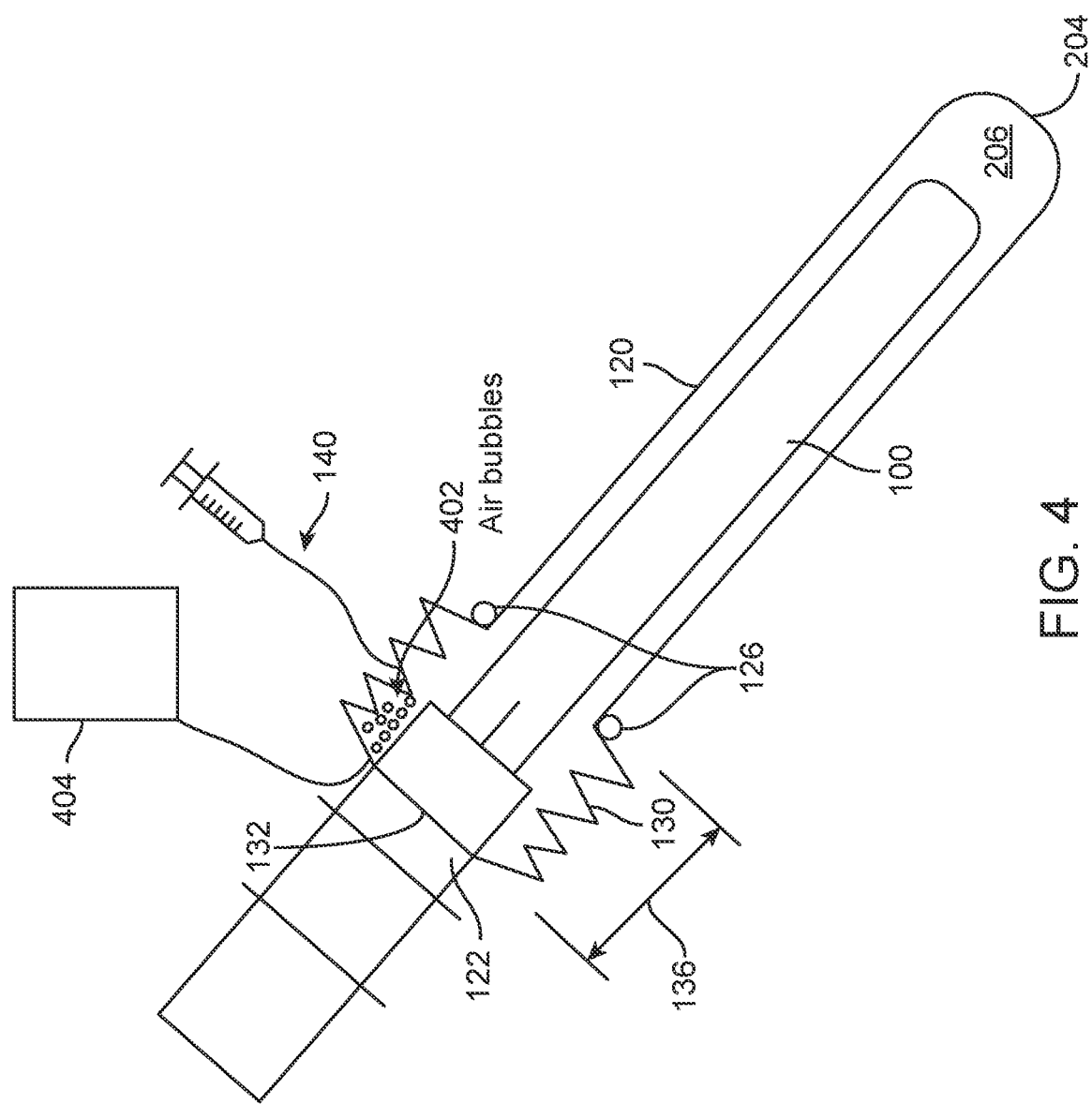
FIG. 4 shows an imaging probe in a stiff sheath connected to fluid sources, in accordance with some embodiments.

FIG. 4 shows an imaging probe in a stiff sheath connected to fluid sources. The stiff sheath 120 may be coupled to the probe 100 by a flexible coupling 130. The flexible coupling 130 may provide a fluid tight seal 132 between the coupling 130 and the imaging probe 100. The arm 126 can engage the stiff sheath 120 as described herein. The proximal and distal movement of the probe 100 can change the distance 136 of the coupling as described herein. The flexible coupling 130 may be removably coupled to the imaging probe 100, such that the stiff sheath 120 may be replaced between subsequent procedures while allowing the imaging probe 100 to be reused. The flexible coupling 130 may be connected to the probe 100 by any suitable structure, mechanism, or method. Some suitable examples, which may comprise seal 132, include a band clamp, an adhesive, a ratchet strap, an O-ring, a deformable membrane, a spring clip, gland packing, a gasket, a reciprocating seal, a crown gasket, a crown seal, a U-cup, or any other suitable sealing structure or combinations thereof.

A fluid source 140 may be provided and be in fluid communication with chamber 206. The fluid source 140 may be coupled to the flexible coupling 130 through any suitable fluid tight seal. During initial loading of the stiff sheath 120 with ultrasound fluid from the fluid source 140, a volume of gas may be present within the chamber 206. As the ultrasound fluid is introduced into the chamber 206, the gas may form bubbles 402 within the fluid. The stiff sheath 120 and probe 100 may initially be oriented such that the distal end portion 204 comprising the chamber 206 is below the flexible coupling 130 so as to encourage the fluid to flow toward the chamber 206 and the sheath distal end portion 204.

As gas bubbles 402 form in the fluid, orienting the assembly in the illustrated downward orientation will encourage the bubbles 402 to flow upwards toward the flexible coupling 130. In some embodiments, the bubbles are able to escape through the flexible coupling 130, such as by entering the fluid source 140. Optionally, a second source 404 of flowable material may be provided to aid with initial loading of the stiff sheath 120, with evacuation of gas from the stiff sheath 120, or some other purpose. In some embodiments, the gas bubbles can flow toward either the first fluid source 140, the second source 404 of flowable material, or both. In some embodiments, gas bubbles are encouraged to coalesce within the flexible coupling and may optionally be removed. The first fluid source 140, the second source 404 of flowable material, or both, comprise a low viscosity and low surface tension material to provide a low resistance movement and evacuation of air bubbles from the internal chamber of the stiff sheath. With the gas collecting in the flexible coupling 130, the imaging probe 100 may acquire imaging data from within the patient, for example without the gas causing degradation in the images.

As the imaging probe 100 moves within the stiff sheath 120, fluid may be drawn into the chamber 206 as the imaging probe moves proximally in the stiff sheath 120 away from the distal end portion 204. Fluid may be expelled as the imaging probe 100 moves distally within the stiff sheath 120 toward the distal end portion 204. In some embodiments, the first fluid source 140 or the second source 404 of flowable material, or both, allow one-way fluid flow. For example, fluid may flow into the chamber 206 from the first fluid source 140 and may flow out of the chamber into the second source of flowable material 404, or vice versa.

Figure 5:
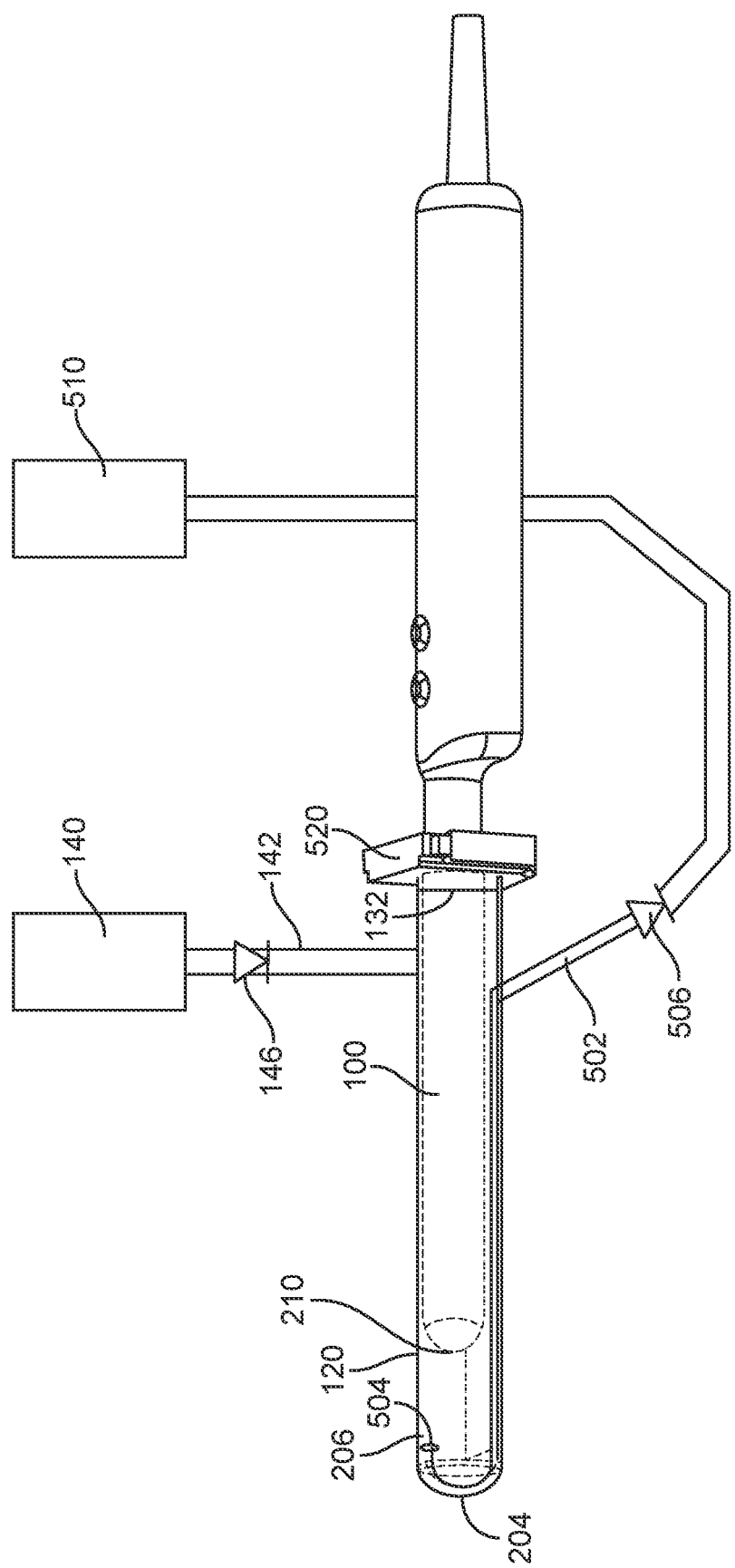
FIG. 5 show an imaging probe in a stiff sheath with an outlet line, in accordance with some embodiments.

FIG. 5 show an imaging probe 100 in a stiff sheath 120 with an outlet line 502. In some embodiments, the outlet line 504 comprises a bleed line. The imaging probe and stiff sheath may comprise one or more components as described herein, such as the seal 132 and coupling 130, for example. The imaging probe can be mounted on an arm as described herein. Upon initial insertion of the imaging probe 100 into the stiff sheath 120, a volume of gas may be present within the stiff sheath 120. As the stiff sheath is advanced distally, the volume of the chamber 206 reduces and forces gas toward the sheath distal end portion 204. Moreover, gas bubbles will tend to migrate upwards. Work in relation to the present procedure suggests that during surgery such as prostate surgery, bubbles would tend to collect on an upper side of the probe toward the distal end portion 204.

In some embodiments, an outlet line 502 is formed within the chamber 206 and comprises one or more openings 504 that allows gas to enter. The one or more openings 504 may be formed near an upper surface of the stiff sheath 120, such that bubbles will tend to migrate upwardly toward the one or more openings 504. Insertion of the imaging probe 100 into stiff sheath 120 will further encourage the bubbles to enter the outlet line 502 through the one or more openings 504. In some embodiments, the outlet line 502 extends away from one or more openings 504 located near an upper surface of the stiff sheath 120. The outlet line may follow the curvature of the sheath distal end portion 204 and may exit the sheath 120 at any suitable location.

The one or more openings 504 can be located at any suitable location within stiff sheath 120. Work in relation to the present disclosure suggests that the distal tip of the probe 100 and the distal end portion 204 may be inclined upwardly with respect to the proximal end of the probe and sheath. In this regard, the one or more openings can be located on an upper interior surface of sheath 120, in which the one or more openings corresponds to an upper most position of the probe when inclined upwardly at an angle within a range from about 1 degree to about 20 degrees. Also, the probe may comprise an indicia or other structure to align the vertical axis of the probe with the arm as described herein. In some embodiments, the sheath 120 comprises an alignment structure 520 configured to place the sheath 120 on the arm at a predetermined registration angle, e.g. so as to position the one or more openings 504 vertically. The arm may comprise a corresponding structure to engage the alignment structure 520 of the sheath so as to set the rotational angle of the sheath about the elongate axis of the probe 100.

Although reference is made to outlet line 502 extending within chamber 206, in some embodiments outlet line 520 extends along an exterior of the stiff sheath 120. Alternatively or in combination, stiff sheath 120 may comprise outlet line 502 extending between an interior surface and an exterior surface of the stiff sheath 120.

In some embodiments, the outlet line 502 comprises a valve 506, that allows gas to flow through the outlet line 502 and exit through the valve 506. The valve 506 may comprise any suitable valve, such as a one-way valve, e.g. a check valve. In some embodiments, the imaging probe 100 and stiff sheath 120 system is primed before using the imaging probe to capture imaging data. For example, a flowable material may be introduced into the stiff sheath 120. The imaging probe 100 may be advanced into the stiff sheath 120 and gas within the stiff sheath 120 flows through the outlet line 502 and exits the system after passing through the valve 506. In some embodiments, the outlet line 502 extends to a reservoir 510, which is configured to store flowable material from line 502. In some embodiments, reservoir 510 is located above the stiff sheath 120 to decrease siphoning of the chamber of the stiff sheath. Alternatively, line 502 can bleed directly into a receptacle for surgical waste, depending on the viscosity of the flowable material.

In some embodiments, fluid source 140 is coupled to the interior of the stiff sheath 120 with a line 142. The line 142 can be coupled to the interior of the stiff sheath with an opening at one or more of many locations, for example proximally or distally near the end. In some embodiments, the line 142 is coupled to the interior of the stiff sheath with an opening at a location that is beneath the one or more openings 504 when the sheath has been placed in the patient with the distal tip of the sheath inclined slightly upwardly relative to the proximal end as described herein. The fluid source 140 may comprise a gel or other suitable flowable material. In some embodiments, fluid source 140 is located above reservoir 510 in order to provide a continuous flushing flow to the stiff sheath 120. In some embodiments, this flushing will direct bubbles away from the distal tip, for example when probe 100 remains stationary. In some embodiments, the fluid source 140 is allowed to equilibrate with the reservoir 510 prior to pumping, for example, so as to remove air from the stiff sheath 120.

In some embodiments, the imaging probe 100 will be reciprocated within the stiff sheath 120 one or more times to draw in additional fluid from a fluid source and expel gas through the outlet line. In this way, gas within the stiff sheath 120 is replaced with a flowable material comprising an acoustic medium such as an ultrasound gel or saline.

In some embodiments, inlet line 142 is coupled to fluid source 140 with a one-way valve such as a check valve 146. The check valve 146 can allow fluid to be drawn from fluid source 140 and into the interior channel of the stiff sheath 120 when the probe is drawn proximally away from the distal end of the stiff sheath. When the probe is advanced distally into the stiff sheath 120, the check valve will substantially block fluid flow from the internal channel toward the fluid source 140 and direct fluid toward the one or more openings 504 and out the outlet line 502.

In some embodiments, the fluid source includes a delivery line coupled to a one-way valve, such that translating the imaging probe 100 in a withdrawing direction will draw in fluid from the fluid source, and translating the imaging probe 100 in an advancing direction within the stiff sheath 120 will expel gas and fluid through the bleed valve. The imaging probe 100 may be reciprocated one or more times to draw in sufficient fluid to fill the chamber 206 and expel any gas within the chamber 206. In some embodiments, reciprocation of the imaging probe 100 acts as a pump to draw in an initial volume of fluid in order to fill the chamber prior to performing imaging or treatment. In some embodiments, vacuum probe resistance is decreased (and optionally minimized) during advancement and/or retraction of the probe within the sheath (optionally pistoning) with one or more of venting at a distal end of the sheath 120 or delivery of flowable material filling a vacuum generated with retraction of the probe 100 in the sheath 120 or utilizing low viscosity fluid which will travel along the gap between the sheath and the probe.

In some embodiments, the sheath 120, the valve 506, the probe 100 and fluid source 140 are arranged in a fluid recirculating configuration. For example, the line 502 comprising one-way valve 506 can be connected to the fluid source 140, in order to recirculate the fluid. The output fluid from line 502 can be input into fluid source 140 near an upper portion of the container, for example, so as to separate gas in line 502 from liquid in line 502. The line 142 can be coupled to fluid source 140 at a lower location than the input from line 502 so as to separate the ultrasound fluid from gas prior to drawing fluid from source 140 into sheath 120.

Figure 6:
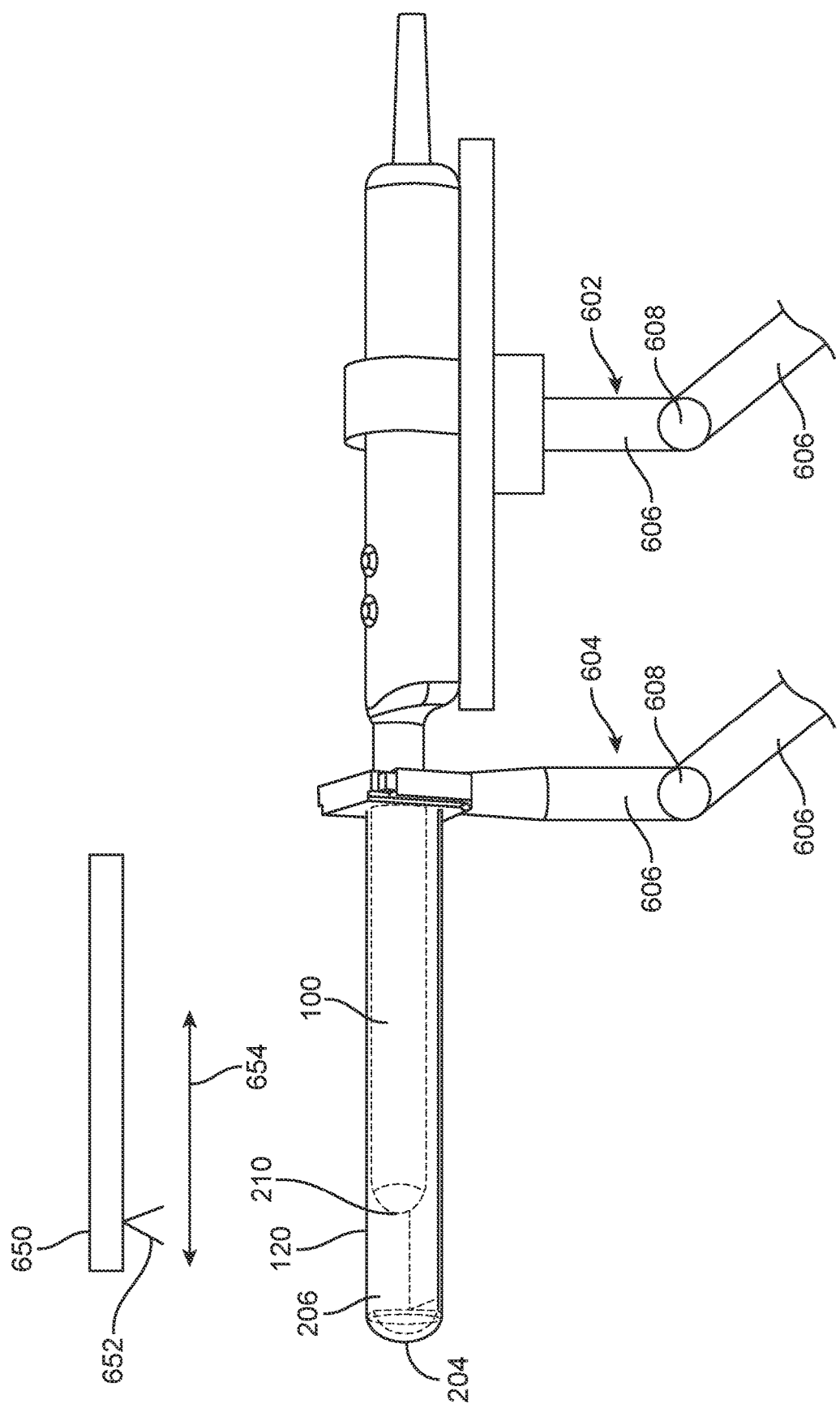
FIG. 6 shows a stiff sheath supported by a first robotic arm and an imaging probe supported by a second robotic arm, in accordance with some embodiments.

FIG. 6 shows an imaging probe 100 supported by a first robotic arm 602 and a stiff sheath 120 supported by a second robotic arm 604. The stiff sheath 120 as described herein, may be coupled to a robotic arm 604, which may be configured to move and position the stiff sheath 120 under control of a processor and user input. Moreover, the second robotic arm 604 may be configured to move and position the stiff sheath 120 independently of the imaging probe 100. The imaging probe 100 may be coupled to a first robotic arm 602, which may move, orient, and position the imaging probe 100 under control of a processor. The imaging probe 100 may move independently of the stiff sheath 120.

The robotic arms as described herein can be configured in many ways, and may comprise from 5 to 8 joints, for example from 5 to 7 joints and may comprises commercially available robotic arms. In some embodiments, the distal end of the robotic arm is configured to position the probe with from 3 to 6 degrees of freedom, for example with 6 degrees of freedom. In some embodiments, the 6 degrees of freedom comprise three translational degrees of freedom and three rotational degrees of freedom.

In some embodiments, the stiff sheath 120 is moved and positioned to a patient by the second robotic arm 604. Subsequently, the first robotic arm 602 may move the imaging probe 100 to enter the stiff sheath 120 and prepare for capturing imaging data. In some embodiments, the first robotic arm 602 inserts and advances the imaging probe 100 into the stiff sheath 120 outside of a patient before a procedure. Under control of one or more processors, the first robotic arm 602 and second robotic arm 604 may prepare the imaging probe 100 and stiff sheath 120 for a procedure, such as by inserting the imaging probe 100 into the stiff sheath 120, priming the system with flowable material as described elsewhere herein, and position the imaging probe 100 and stiff sheath 120 together within a patient at a target location.

The robotic arms may be any suitable robotic arms and may comprise one or more linkages 606 coupled with robotic joints 608. The robotic arms may be fully under the guidance of a processor, or may offer selective manual user control. For example, a physician may manually guide the first robotic arm 602, the second robotic arm 604, or both before or during a procedure. In some cases, a physician may manually control the robotic arms to prepare the imaging probe 100 and stiff sheath 120 for a procedure, such as by priming the stiff sheath 120 with fluid and inserting the imaging probe 100 into the stiff sheath. The physician may also elect to manually place the stiff sheath 120, the imaging probe 100, or both into an initial position within a patient. The physician may then cause the processor to execute instructions that cause the processor to operate the first robotic arm 602, the second robotic arm 604, the motor of the imaging probe 100, or a combination. In some instances, the first robotic arm 602 is responsible for advancing and retracting the imaging probe 100 during a procedure. The first robotic arm 602 may also be configured to rotate the imaging probe 100 about its longitudinal axis, as desired.

In some embodiments, a treatment probe 650 is configured to one or more of resect or ablate tissue. The treatment probe comprises an energy source 652. The energy source may comprise any suitable energy source, such as a water jet, a laser beam, one or more RF electrodes, or a laser beam transmitted along a water stream, and combinations thereof. The treatment probe 650 can be configured to move the energy source with a translational movement 654, or a rotational movement, and combinations thereof. In some embodiments, the treatment probe 650 is mounted on a third robotic arm, which may be similar to the first robotic arm and the second robotic arm.

In some embodiments, it may be helpful to move the imaging probe 100 with the treatment probe 650 so as to maintain the energy source within the field of view of the imaging probe 100. In some embodiments, the imaging probe 100 is configured to move synchronously with the treatment probe 650, for example with synchronous translational movement 654. In some embodiments, the stiff sheath 120 and probe 100 pump fluid as described herein during the translational movement of the treatment probe.

In some embodiments the robotic arm 604 maintains the position and orientation of the stiff sheath 120 while the robotic arm 602 translates the probe 100 inside the stiff sheath 120 with movement and optional pumping as described herein.

The robotic arms 602, 604 and the treatment probe 650 can be coupled to a suitable controller, processor and linkage as will be known to one of ordinary skill in the art. Systems suitable for incorporation in accordance with present disclosure are described in International Application No. PCT/US2013/028441, filed Feb. 28, 2013, published as WO2013/130895 on Sep. 6, 2013 entitled "AUTOMATED IMAGE-GUIDED TISSUE RESETION AND TREATMENT", and International Application No. PCT/US2014/054412, filed Sep. 5, 2014, published as WO2015/035249 on Mar. 12, 2015, entitled "AUTOMATED IMAGE-GUIDED TISSUE RESETION AND TREATMENT", the entire disclosures of which have been previously incorporated by reference.

Figure 7:
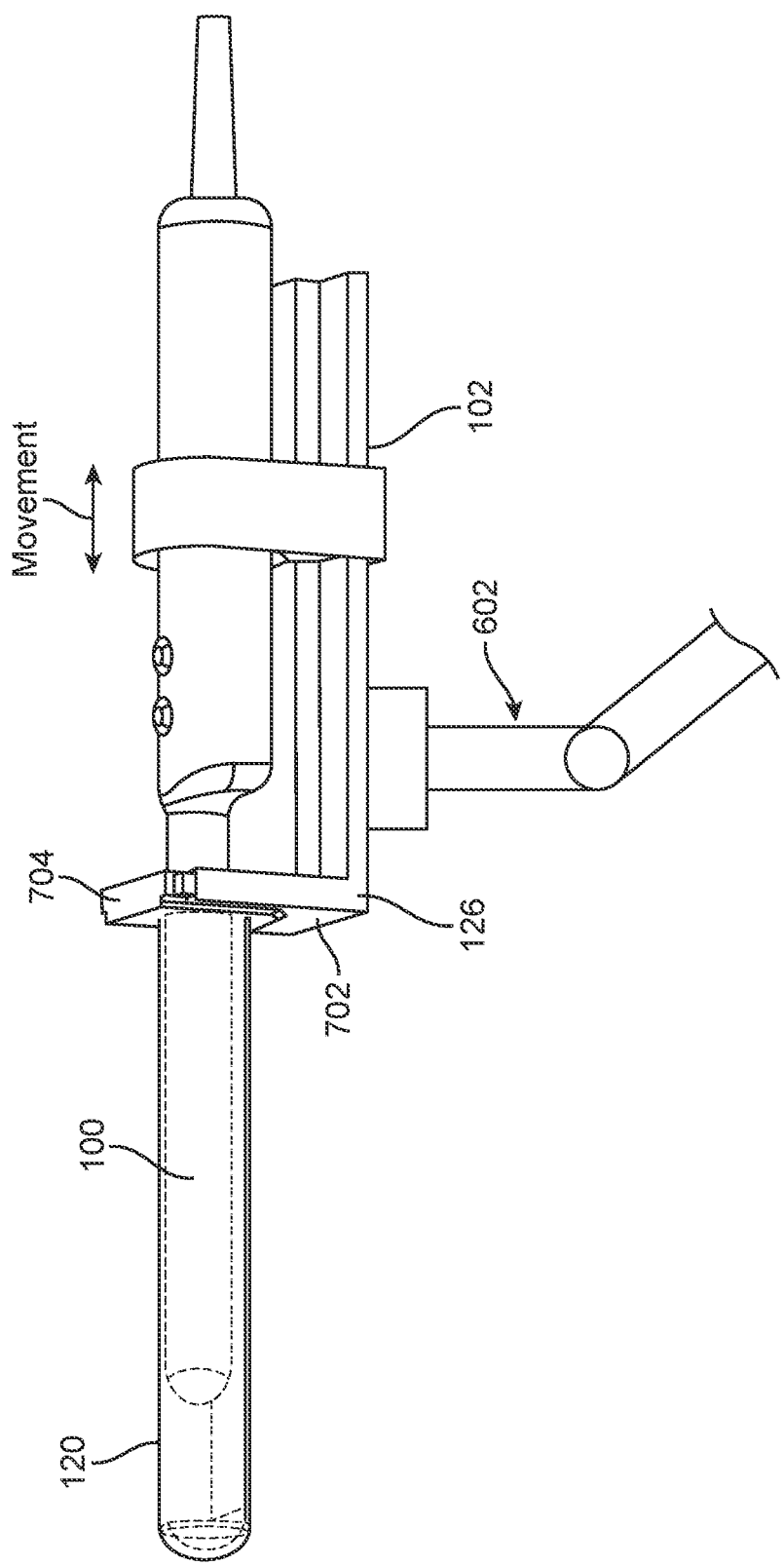
FIG. 7 shows a side view of a stiff sheath over an imaging probe coupled to a common base that is carried by a robotic arm, in accordance with some embodiments.

FIG. 7 illustrates a side view of a stiff sheath 120 over an imaging probe 100 coupled to a common base that is carried by a robotic arm. The imaging probe 100 and stiff sheath 120 may be carried by the base 102 and function similarly to the probe 100 described with reference to FIG. 1. The base 102 can be coupled to a carriage that allows translation of the imaging probe 100 relative to the common base 102. The common base 102 may comprise an arm 126 that includes an extension 702 that couples to a proximal end 704 of the stiff sheath 120 as described herein. The coupling of the proximal end 704 of the stiff sheath 120 and the extension 702 may be by any suitable connection system, such as cooperating structure, a boss and groove, a sliding dovetail, a magnetic coupling, a retaining clip, a clamp, or some other suitable connection.

The base 102 may be coupled to a robotic arm 602. The robotic arm 602 may be under control of one or more processors that can instruct the robotic arm to move, position, and orient the imaging probe 100 and stiff sheath 120. The robotic arm can locate the stiff sheath 120 and imaging probe 100 assembly at a target site within a patient. An actuator, such as a stepper motor, may move the imaging probe 100 independently of the stiff sheath 120 such as for capturing imaging data, while the stiff sheath 120 maintains the surrounding tissue in a static position while the imaging probe 100 translates.

Figure 8:
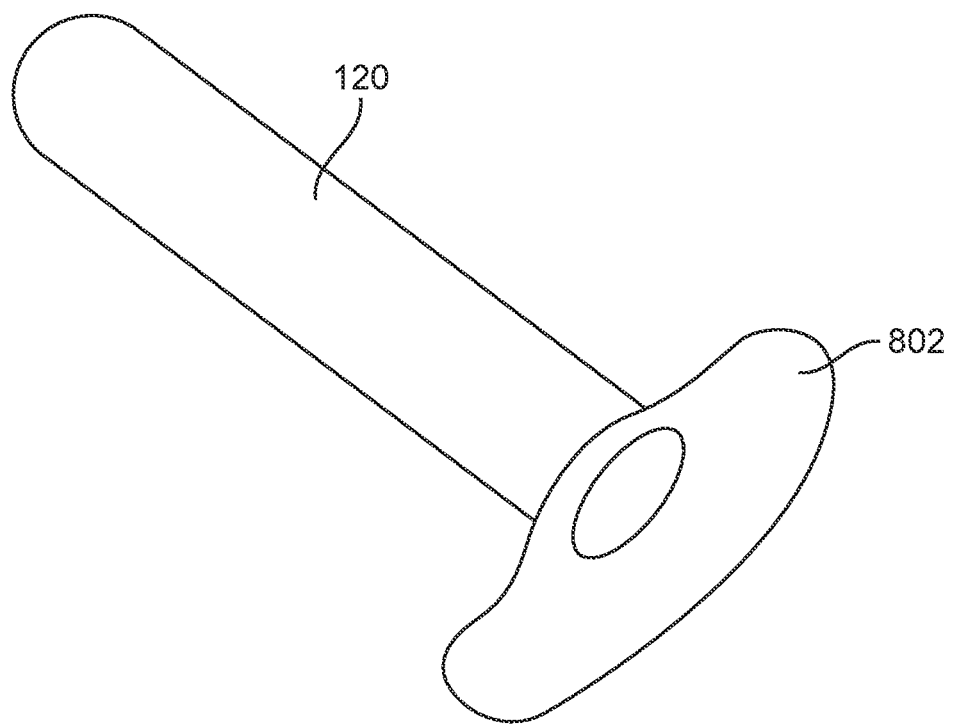
FIG. 8 shows a perspective view of a stiff sheath having protrusions such as wings, in accordance with some embodiments.

FIG. 8 shows a perspective view of a stiff sheath 120 having protrusions such as wings 802. In some embodiments, the stiff sheath 120 may be attached to a patient, and in some cases, is configured with wings 802. The wings 802 may comprise protrusions that provide a positive stop and inhibit further insertion of the stiff sheath 120 into a patient, for example. The wings 802 may additionally provide a surface that contacts the patient around the entry location of the TRUS probe and allows the wings to be secured to the patient, such as by surgical tape. In this embodiment, the stiff sheath 120 can be positioned and secured within the patient prior to the start of a treatment and the imaging probe can subsequently be inserted into the stiff sheath 120. The stiff sheath 120 may comprise the coupling, seal, check valve, and openings as described herein.

In use, the stiff sheath 120 is coupled to the arm, probe, actuator, the base of the apparatus, or directly to the patient. A probe 100 is inserted through the flexible coupling of the sheath 120 and the sheath may be sealed to provide a fluid-tight seal between the sheath 120 and the probe 100 as described herein. The ultrasound probe may be connected to the actuator as described herein.

The assembly may be oriented with the distal end of the probe 100 facing downward, or may be positioned in this orientation in preparation for connection with one or more fluid sources. This orientation can be used to introduce flowable material into the sheath 120, for example prior to advancement of the probe 100 into the sheath 120. The fluid source may be fluidically connected to the interior of the sheath 120, such as by attaching a fluid hose associated with the fluid source to a fluid coupling positioned at the flexible coupling. In some embodiments, the fluid source is positioned at a higher elevation than the apparatus to allow gravity to encourage the flowable material to flow downward into the sheath 120.

The probe 100 may be positioned within the sheath 120 either manually or by the actuator, by a robotic arm, or through a combination thereof. Advancing the probe 100 into the sheath 120 can push air, liquid and other flowable material out of the sheath 120 through an evacuation pathway and draw fluid from the fluid source into the sheath 120. Gravity can cause the fluid to migrate toward the distal end of the sheath 120 and any gas bubbles will float toward the proximal end of the probe 100 out of the targeting area. In some cases, the gas bubbles can be withdrawn from the sheath such as by evacuating the gas bubbles, or the probe 100 can be repeatedly inserted and withdrawn from the sheath 120 to encourage any gas bubbles to exit the sheath 120.

While the probe and sheath have been described as having a diameter, it should be appreciated that the sheath and probe need not have a generally circular cross section, but could be ovoid, hexagonal, octagonal, or some other shape. In many embodiments, the probe is configured to rotate about its longitudinal axis without disturbing the position or orientation of the sheath, so in many embodiments, the sheath has a generally circular cross-sectional shape.

The present disclosure includes the following numbered clauses.

Clause 1. An imaging system to image tissue of a patient, comprising: an imaging probe to be inserted into the patient; a stiff sheath, the stiff sheath comprising an internal channel sized to receive the imaging probe; and a seal to inhibit leakage of fluid from an interior of the stiff sheath.

Clause 2. The imaging system of clause 1, wherein the seal is configured to inhibit air from entering the interior of the sheath when the probe has been inserted into the sheath and the probe is drawn proximally away from a distal end of the sheath.

Clause 3. The imaging system of clause 1, wherein the seal is configured to inhibit liquid from exiting the interior of the sheath when the probe has been inserted into the sheath and the probe is advanced distally toward a distal end of the sheath.

Clause 4. The imaging system of clause 1, wherein the internal channel comprises an elongate axis and the imaging probe comprises an elongate axis, and wherein the stiff sheath is configured to resist deformation when the elongate imaging probe is drawn proximally.

Clause 5. The imaging system of clause 1, wherein the internal channel of the sheath comprises an internal diameter dimensioned to receive the imaging probe, and with a gap of no more than about 1 mm between an external surface of the imaging probe and an internal diameter of the sheath.

Clause 6. The imaging system of clause 1, wherein the seal comprises a flexible seal coupling the imaging probe to the stiff sheath, the flexible seal creating a fluid tight seal between the imaging probe and the stiff sheath.

Clause 7. The imaging system of clause 6, wherein the flexible seal comprises a bellows.

Clause 8. The imaging system of clause 6, wherein the flexible seal comprises a sliding seal.

Clause 9. The imaging system of clause 1, further comprising an evacuation channel in fluid communication with an interior chamber of the stiff sheath.

Clause 10. The imaging system of clause 9, further comprising a check valve coupled to the evacuation channel to provide one-way fluid flow through the evacuation channel.

Clause 11. The imaging system of clause 10, wherein the one-way fluid flow causes fluid to flow out of the interior chamber of the stiff sheath.

Clause 12. The imaging system of clause 10, further comprising a reservoir to receive fluid from the check valve.

Clause 13. The imaging system of clause 12, wherein the reservoir is located above the internal channel.

Clause 14. The imaging system of clause 13, further comprising an inlet line coupled to a fluid source and the internal channel to provide fluid to the internal channel when the probe is drawn proximally away from a distal end of the sheath.

Clause 15. The imaging system of clause 14, wherein the reservoir comprises the fluid source and wherein the sheath, the probe, the check valve, the gasket, the inlet line and the outlet line are arranged as a recirculating pump.

Clause 16. The imaging system of clause 1, further comprising a fluid source coupled to the internal channel of the stiff sheath between the seal and a distal end of the stiff sheath.

Clause 17. The imaging system of clause 16, wherein the fluid source is located above the internal channel.

Clause 18. The imaging system of clause 1, wherein the stiff sheath comprises a cylinder and the probe comprise a piston and wherein the cylinder and the piston are arranged to pump fluid with reciprocal motion of the probe in the sheath.

Clause 19. The imaging system of clause 18, wherein the seal is located on the imaging probe and optionally wherein the seal comprises one or more rings placed on the imaging probe.

Clause 20. The imaging system of clause 1, further comprising a line to remove fluid from the internal channel, the line extending to one or more openings within the internal channel.

Clause 21. The imaging system of clause 20, wherein the one or more openings are located on an upper side of the internal channel to receive air bubbles.

Clause 22. The imaging system of clause 21, wherein the one or more openings are located near a distal tip of the imaging probe.

Clause 23. The imaging system of clause 22, wherein the one or more openings are located along an upper interior surface of the internal channel.

Clause 24. The imaging system of clause 23, wherein the stiff sheath comprises a reference structure to orient the stiff sheath with the one or more openings along the upper interior surface.

Clause 25. The imaging system of clause 24, further comprising a support arm to support the stiff sheath, the support arm comprising an engagement structure corresponding to the reference structure to receive the stiff sheath with the one or more openings oriented along the upper interior surface.

Clause 26. The imaging system of clause 1, further comprising a flexible coupling coupled to the seal.

Clause 27. The imaging system of clause 26, wherein the flexible coupling comprises a first end portion configured to engage the stiff sheath at a first location, and a second end portion to engage the probe at a second location of the flexible coupling.

Clause 28. The imaging system of clause 27, wherein a distance extends between the first location and the second location and wherein the distance decreases when the probe is advanced into the internal channel and the distance increases when the probe is retracted from the internal channel.

Clause 29. The imaging system of clause 27, wherein the flexible coupling comprises an internal volume of fluid and wherein the internal volume increases when the probe is advanced into the stiff sheath and the internal volume decreases when the probe is retracted away from a distal end of the internal channel.

Clause 30. The imaging system of clause 29, wherein the flexible coupling comprises a balloon, the balloon adhered to the stiff sheath at the first location and coupled to the probe at the second location to form the seal.

Clause 31. The imaging system of clause 29, wherein the flexible coupling comprises a bellows.

Clause 32. An imaging system to image tissue of a patient, comprising: an imaging probe to be inserted into the patient; a stiff sheath, the stiff sheath comprising an internal channel sized to receive the imaging probe; and an outlet line to remove fluid from the internal channel, the line extending to one or more openings within the internal channel, wherein the one or more openings are located on an upper side of the internal channel to receive air bubbles.

Clause 33. The imaging system of clause 32, wherein the one or more openings are located near a distal tip of the imaging probe.

Clause 34. The imaging system of clause 33, wherein the one or more openings are located along an upper interior surface of the internal channel.

Clause 35. The imaging system of clause 34, wherein the stiff sheath comprises a reference structure to orient the stiff sheath with the one or more openings along the upper interior surface.

Clause 36. The imaging system of clause 32, wherein the external surface of the probe and the internal surface of the stiff sheath are dimensioned to seal the interior channel and wherein the internal channel extends to a fluid reservoir.

Clause 37. The imaging system of clause 36, wherein the external surface of the probe and the internal surface of the stiff sheath are dimensioned to seal the internal channel and wherein the outlet line extends to a fluid reservoir.

Clause 38. The imaging system of clause 37, wherein the outlet line comprises a one-way valve to pump fluid into the reservoir.

Clause 39. The imaging system of clause 37, wherein an inlet line from a fluid source extends to the internal channel.

Clause 40. The imaging system of clause 39, wherein the inlet line comprises a one-way valve to inhibit flow toward the fluid source and to direct fluid through the one or more openings when the probe advances in the stiff sheath.

Clause 41. A system to treat a patient, comprising: the imaging probe of any one of the preceding clauses; and a treatment probe comprising a source of energy.

Clause 42. The system of clause 41, wherein the imaging probe is configured to move synchronously with a carrier of the treatment probe.

Clause 43. The imaging system of clause 1, further comprising a stiff sheath and imaging probe assembly, the assembly configured to replace air in the stiff sheath with an acoustic medium.

Clause 44. The system, imaging probe or assembly of any one of the preceding clauses, wherein an acoustic medium comprises a low viscosity and low surface tension to provide a low resistance movement and evacuation of air bubbles from the internal channel of the stiff sheath and optionally wherein the acoustic medium comprises a flowable material and optionally wherein the flowable material comprises a liquid or a gel.

Clause 45. The system, imaging probe or assembly of any one of the preceding clauses, wherein vacuum probe resistance is decreased during advancement and/or retraction of the probe in the sheath with one or more of venting near a distal end of the sheath, delivery of flowable material filling a vacuum generated with retraction of the probe in the sheath, or utilizing low viscosity fluid which will travel along a gap between the sheath and the probe.

Clause 46. The system, imaging probe or assembly of any one of the preceding clauses, further comprising a lumen from a syringe to the sheath with fluid conducted along the bottom or side (away from the viewing area) of the stiff sheath, said lumen configured to deliver acoustic fluid into the stiff sheath and surround the ultrasound probe to provide acoustic coupling from the probe to the sheath with the fluid disposed in between.

Clause 47. The system, imaging probe or assembly of any one of the preceding clauses, wherein an arm is configured to support the stiff sheath and the imaging probe and wherein a linkage supported with the arm is configured to translate the imaging probe to a plurality of locations within the stiff sheath and to rotate the imaging to a plurality of orientations within the stiff sheath.

Clause 48. The system, imaging probe or assembly of clause 47, wherein the arm comprises a robotic arm configured to position the imaging probe and the stiff sheath and optionally wherein the robotic arm comprises from 5 to 7 degrees of freedom.

Clause 49. The system, imaging probe or assembly of any one of the preceding clauses, wherein a robotic arm is configured to support the stiff sheath and to position the stiff sheath with three translational degrees of freedom and three rotational degrees of freedom and optionally wherein the robotic arm comprises from 5 to 7 degrees of freedom.

Clause 50. The system, imaging probe or assembly of any one of the preceding clauses, wherein a robotic arm is configured to support the imaging probe and to position the imaging probe with three translational degrees of freedom and three rotational degrees of freedom.

Clause 51. A system for imaging tissue, comprising: a first robotic arm configured to support a stiff sheath and to position the stiff sheath with three translational degrees of freedom and three rotational degrees of freedom; and a second robotic arm configured to support the imaging probe and to position the imaging probe with three translational degrees of freedom and three rotational degrees of freedom; wherein second robotic arm is configured to place the imaging probe in the stiff sheath.

Clause 52. The system of clause 51, further comprising the imaging system of any one of the preceding clauses.

Clause 53. A method, the method comprising using the system of any one of the preceding clauses.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof

What is claimed is:

1. An imaging system to image tissue of a patient, comprising:
    an imaging probe to be inserted into the patient;
    a stiff sheath, the stiff sheath comprising an internal channel sized to receive the imaging probe and a closed distal end, wherein the closed distal end is rounded for advancement into the patient;
    a proximal seal to decrease leakage of fluid from an interior of the stiff sheath;
    a fluid source coupled to the interior of the stiff sheath;
    a one-way valve between the fluid source and the interior of the stiff sheath configured to allow fluid from the fluid source to flow into the interior of the stiff sheath;
    an evacuation channel in fluid communication with an interior chamber of the stiff sheath; and
    a check valve coupled to the evacuation channel to provide one-way fluid flow through the evacuation channel;
    wherein the stiff sheath and the imaging probe are sized and arranged to pump fluid with a reciprocating motion of the imaging probe in the stiff sheath.

2. The imaging system of claim 1, wherein the proximal seal is configured to inhibit air from entering the interior of the stiff sheath when the imaging probe has been inserted into the stiff sheath and the imaging probe is drawn proximally away from the closed distal end of the stiff sheath.

3. The imaging system of claim 1, wherein the proximal seal is configured to inhibit liquid from exiting the interior of the stiff sheath when the imaging probe has been inserted into the stiff sheath and the imaging probe is advanced distally toward the closed distal end of the stiff sheath.

4. The imaging system of claim 1, wherein the internal channel comprises an elongate axis and the imaging probe comprises an elongate axis, and wherein the stiff sheath is configured to resist deformation when the imaging probe is drawn proximally.

5. The imaging system of claim 1, wherein the internal channel of the stiff sheath comprises an internal diameter dimensioned to receive the imaging probe, and with a gap of no more than about 1 mm between an external surface of the imaging probe and the internal diameter of the stiff sheath.

6. The imaging system of claim 1, wherein the proximal seal comprises a flexible seal coupling the imaging probe to the stiff sheath, the flexible seal creating a fluid tight seal between the imaging probe and the stiff sheath.

7. The imaging system of claim 6, wherein the flexible seal comprises a bellows.

8. The imaging system of claim 6, wherein the flexible seal comprises a sliding seal.

9. The imaging system of claim 1, further comprising the fluid source coupled to the internal channel of the stiff sheath between the proximal seal and the closed distal end of the stiff sheath.

10. The imaging system of claim 9, wherein the fluid source is located above the internal channel.

11. The imaging system of claim 1, wherein the stiff sheath comprises a cylinder and the imaging probe comprise a piston and wherein the cylinder and the piston are arranged to pump fluid with the reciprocating motion of the imaging probe in the stiff sheath.

12. The imaging system of claim 11, wherein the proximal seal is located on the imaging probe and wherein the proximal seal comprises one or more rings placed on the imaging probe.

13. The imaging system of claim 1, further comprising a line to remove fluid from the internal channel, the line extending to one or more openings within the internal channel.

14. The imaging system of claim 13, wherein the one or more openings are located on an upper side of the internal channel to receive air bubbles.

15. The imaging system of claim 1, further comprising a flexible coupling coupled to the proximal seal.

16. The imaging system of claim 15, wherein the flexible coupling comprises a first end portion configured to engage the stiff sheath at a first location, and a second end portion to engage the imaging probe at a second location of the flexible coupling.

17. The imaging system of claim 16, wherein a distance extends between the first location and the second location and wherein the distance decreases when the imaging probe is advanced into the internal channel and the distance increases when the imaging probe is retracted from the internal channel.

18. The imaging system of claim 16, wherein the flexible coupling comprises an internal volume of fluid and wherein the internal volume increases when the imaging probe is advanced into the stiff sheath and the internal volume decreases when the imaging probe is retracted away from a distal end of the internal channel.

19. The imaging system of claim 1, wherein the stiff sheath comprises a cylindrical sleeve and the imaging probe comprises a piston sized and configured to slide within the cylindrical sleeve to pump fluid with the reciprocating motion of the imaging probe within the stiff sheath.

20. The imaging system of claim 19, wherein the stiff sheath and the imaging probe are configured to draw in sufficient fluid to fill the interior chamber and expel gas from within the interior chamber by reciprocating the imaging probe within the stiff sheath.

* * * * *